United States Patent
Ades et al.

(10) Patent No.: US 10,167,124 B2
(45) Date of Patent: Jan. 1, 2019

(54) SHAVE CREAM POD

(71) Applicant: Pacific Shaving Company, San Francisco, CA (US)

(72) Inventors: Stanley D. Ades, San Francisco, CA (US); Cynthia C. Sofronas, San Francisco, CA (US)

(73) Assignee: PACIFIC SHAVING COMPANY, San Francisco, CA (US)

( * ) Notice: Subject to any disclaimer, the term of this patent is extended or adjusted under 35 U.S.C. 154(b) by 1 day.

(21) Appl. No.: 15/274,499

(22) Filed: Sep. 23, 2016

(65) Prior Publication Data
US 2018/0086523 A1    Mar. 29, 2018

(51) Int. Cl.

| | |
|---|---|
| *B65D 65/46* | (2006.01) |
| *A61Q 9/02* | (2006.01) |
| *A61K 8/06* | (2006.01) |
| *A61K 8/46* | (2006.01) |
| *A61K 8/36* | (2006.01) |
| *A61K 8/60* | (2006.01) |
| *B65D 75/20* | (2006.01) |
| *B65D 75/30* | (2006.01) |
| *A61K 8/11* | (2006.01) |

(52) U.S. Cl.
CPC .............. *B65D 65/46* (2013.01); *A61K 8/064* (2013.01); *A61K 8/11* (2013.01); *A61K 8/361* (2013.01); *A61Q 9/02* (2013.01); *B65D 75/20* (2013.01); *B65D 75/30* (2013.01)

(58) Field of Classification Search
None
See application file for complete search history.

(56) References Cited

U.S. PATENT DOCUMENTS

| | | | | |
|---|---|---|---|---|
| 5,248,495 | A * | 9/1993 | Patterson ............... | A61K 8/042 424/47 |
| 2002/0137641 | A1 * | 9/2002 | Paul ....................... | A61K 8/046 510/130 |
| 2006/0292106 | A1 * | 12/2006 | Fares ..................... | A61K 8/345 424/73 |
| 2010/0111887 | A1 * | 5/2010 | Senee .................... | A61K 8/046 424/73 |
| 2013/0273277 | A1 * | 10/2013 | Lee ........................ | B65D 65/46 428/35.2 |

FOREIGN PATENT DOCUMENTS

WO    WO 94/09763    * 5/1994

OTHER PUBLICATIONS

Fiume et al. (International Journal of Toxicology 32 (Supplement 1) 595-835 (2013)).*

* cited by examiner

*Primary Examiner* — Patricia Duffy
*Assistant Examiner* — Garen Gotfredson
(74) *Attorney, Agent, or Firm* — Polsinelli PC

(57) ABSTRACT

A shaving cream formulation having one or more surfactants, one or more emulsifying agents, and water, wherein water is present in an amount of less than twenty weight percent based on total weight of the formulation. The shave cream formulation being compatible for use with a water-soluble film enclosure.

18 Claims, 2 Drawing Sheets

SHAVE CREAM POD

FIELD

The present disclosure relates generally to a shaving cream formulation. In particular, the subject matter herein generally relates to a shaving cream formulation compatible with a water-soluble film.

BACKGROUND

Shaving can cause significant irritation to the skin; a shaving lubricant can be added to the area to be shaved in order to facilitate the process. There are many different types of shaving lubricants in use including, but not limited to, creams, foams, soaps, and oils. Shaving lubricants typically produce a significant lather, either through stimulation with a brush or propulsion from an aerosol canister. The lather, along with the lubrication, facilitates the shaving process and protects the skin from discomfort and cuts. Creams are the most commonly used shaving lubricant; shaving creams are typically made up of a mixture of soaps and detergents capable of achieving the necessary lather. Specifically, shaving creams typically consist of an emulsion of oils, surfactants, and a large amount (i.e. 60-80 percent) of water. For example, a standard shave cream formulation can comprise approximately 8 percent stearic acid, 4 percent triethanolamine, 0.5 percent lanolin, 2 percent glycerin, 6 percent polyoxyethylene sorbitan monostearate, and 79.5 percent water.

Most common shave creams are sold and dispensed in tubes or aerosol canisters; however, these can be bulky and difficult to pack during travel.

BRIEF DESCRIPTION OF THE DRAWINGS

Implementations of the present technology will now be described, by way of example only, with reference to the attached figures, wherein.

DETAILED DESCRIPTION

Figure 1:
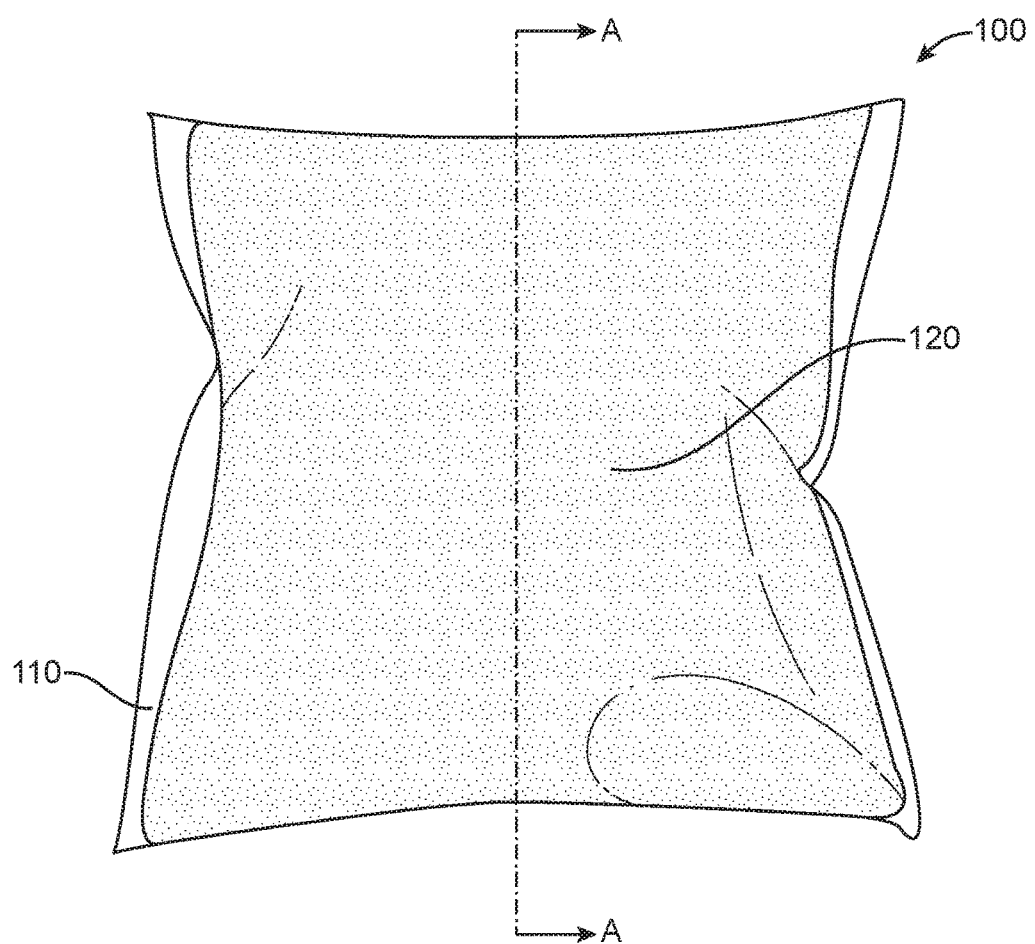
FIG. 1 is a diagram illustrating a first exemplary shave cream pod, according to the disclosure herein.

As described above, typical shave creams can take many forms, including, but not limited to, liquids, lotions, gels, creams, and foams, each of which comprises a plurality of ingredients that work to soften hair and lubricate the skin. Typical shave cream formulations can comprise a combination of surfactants, solvents, humectants, conditioning agents, lubricants, and additives.

Several other industries have begun using single-use dissolvable pods for a variety of reasons. With current travel restrictions for liquids and creams, it would be beneficial to provide a single-use pod containing shave cream. Additionally, single-use pods can significantly reduce waste, as the materials are held in a dissolvable container. However, common shave creams are not compatible with the single-use, dissolvable format, because the high water content of shave creams would dissolve a water-soluble pod from the inside.

Disclosed herein is a shave cream formulation compatible with a water-soluble film enclosure, such as a dissolvable single-use pod. As used herein, "enclosure" is defined as something that encloses, and can be a pod, a pouch, a capsule, a vessel, or the like. To ensure compatibility with presently available water-soluble enclosures, the water content of the shave cream formulation must be less than twenty percent, based on total weight of the formulation. The shave cream formulation disclosed herein can also include, but is in no way limited to, a plurality of surfactants, emulsifiers, humectants, cleansing agents, thickening agents, and a variety of additives.

As used herein, "surfactant" is defined as a compound that lowers the surface tension between two liquids or between a liquid and a solid, the surfactants as described herein can act, for example, as a detergent, a wetting agent, an emulsifier, a foaming agent, or a dispersant. Several different types of surfactants can be used in shave creams including anionic surfactants, such as alkylbenzene sulphonates, alcohol ether sulphates, alcohol sulphates, alkane sulphonates, iesthionates, olefin sulphonates, sarcosinates, soaps, alkyl ethercarboxylates, and sulphosuccinates; nonionic surfactants, such as alkanolamides, amin oxides, fatty amine ethoxylates, polyglucosides, fatty alcohol ethoxylates, fatty alcohol mixed alkoxylates, EO/PO copolymers, and sorbitan esters; cationic surfactants, such as di- and tri-alkyl ammonium salts, and esterquats; and amphoteric surfactants, such as betaines.

The present shave cream can comprise one or more surfactants each selected from ammonium laureth sulfate, ammonium lauryl sulfate, steric acid, triethanolamine myristate, triethanolamine stearate, sodium olefin sulfonate, palmitic acid, sodium laureth sulfate, sodium lauryl sulfate, disodium laureth sulfosuccinate, sodium lauroamphoacetate, laureths 1-23, lauryl glucoside, palm kernel acid, waxes, cocamides, diethanolamine, disodium polyethylene glycol-4-cocoamido monoisopropanolamine sulfosuccinate, lanolin derivatives, coconut acids, polyquaternium compounds, and mixtures thereof. In at least one embodiment, the surfactants can be present in an amount of over about 15 weight percent, based on the total weight of the shave cream formulation; in an alternative embodiment the surfactants can be present in an amount of over 50 weight percent, based on the total weight of the shave cream formulation.

One or more emulsifying agents, or emulsifiers, can also be present in the shave cream formulation. The term "emulsifier", as used herein, is defined as a compound or substance that acts as a stabilizer for emulsions, preventing the liquids from separating. Emulsifiers that can be used in the present shave cream formulation include, but are not limited to, behenyl alcohol, carbomers, communis oil, cellulose gums, cetearyl alcohol, cetyl alcohol, cocoamide diethanolamine/monoethanolamine, cocoamidopropyl betaine, diethanolamine, palm kernel acid, polysorbates 1-85, sodium lauryl sulfate, steric acids, sulfonated oils, triethanolamine, and mixtures thereof. In at least one embodiment, the one or more emulsifiers can be present in an amount of from about 5 weight percent to about 40 weight percent, based on the total weight of the formulation.

The shave cream formulation can additionally include humectants, or other condition ingredients, to lubricate and moisturize the skin during use. As used herein, "humectant" is defined as a hygroscopic substance used to maintain moisture. Humectants suitable for use in the shave cream formulation can include, but are not limited to, triethylene glycol, tripropylene glycol, propylene glycol, diethylene glycol, hexylene glycol, butylene glycol, mineral oil, lanolin, diethanolamine, cocoamide diethanolamine/monoethanolamine, sodium c12-13 pareth sulfate, glycerin, sorbic acid, sorbitol, urea, collagen, guar gums, polyquaternium compounds, and mixtures thereof. In at least one embodiment, one or more humectants can be present in the shave cream formulation in an amount of from about 5 weight percent to about 20 weight percent, based on the total weight of the formulation.

One or more cleansing agents can be present in the shave cream. Suitable cleansing agents can include, but are not limited to, coconut acids, polyethylene glycol 150 distearate, polyethylene glycol 200 hydroxyglycerylpalmitate, sodium cocoyl isethionate, sodium laureth sulfate, and mixtures thereof. In at least one embodiment, the one or more cleansing agents may be present in an amount of less than about 40 weight percent, based on a total weight of the formulation.

One or more solvents can be present in the shave cream; suitable solvents can include, but are not limited to, ammonium xylenesulfonate, benzyl alcohol, butylene glycol, cocoamide diethanolamine/monoethanolamine, diethanolamine, ethyoxydiglycol, glycerin, and mixtures thereof. In at least one embodiment, the one or more solvents can be present in an amount of from about 1 weight percent to about 15 weight percent, based on the total weight of the formulation.

In at least one embodiment, the shave cream formulation can also include one or more additives based on the desired attributes of the final formulation. Additives that can be used in the shave cream formulation can include, but are not limited to, fragrance, preservatives, pH adjusting materials, skin softeners, skin anaesthetics, skin fresheners, thickening agents, binding agents, wetting agents, colorants, plant extracts, essential oil derivatives, antioxidants, antiseptics, disinfectants, vitamins, and mixtures thereof. In at least one embodiment, additives can be present in an amount of from 0 weight percent to about 10 weight percent.

Typical shave creams have approximately 60-80 percent water. However, a water content of that level would dissolve a water-soluble film. Thus, in order to create a shave cream formulation compatible with a water-soluble film pod, the shave cream formulation must have a significantly lower water content. For example, in at least one embodiment, the present shave cream formulation has from about 0 weight percent to about 20 weight percent water, based on total weight of the formulation. In an alternative embodiment, the present shave cream formulation has from about 1 weight percent to about 15 weight percent water, based on the total weight of the formulation. In yet another embodiment, the present shave cream formulation can have from about 1 weight percent to about 8 weight percent water, based on the total weight of the formulation. During preparation, the formulation is heated, evaporating off at least a portion of the water. Thus, the final water content of the formulation can be lower than the original water content.

Figure 2:
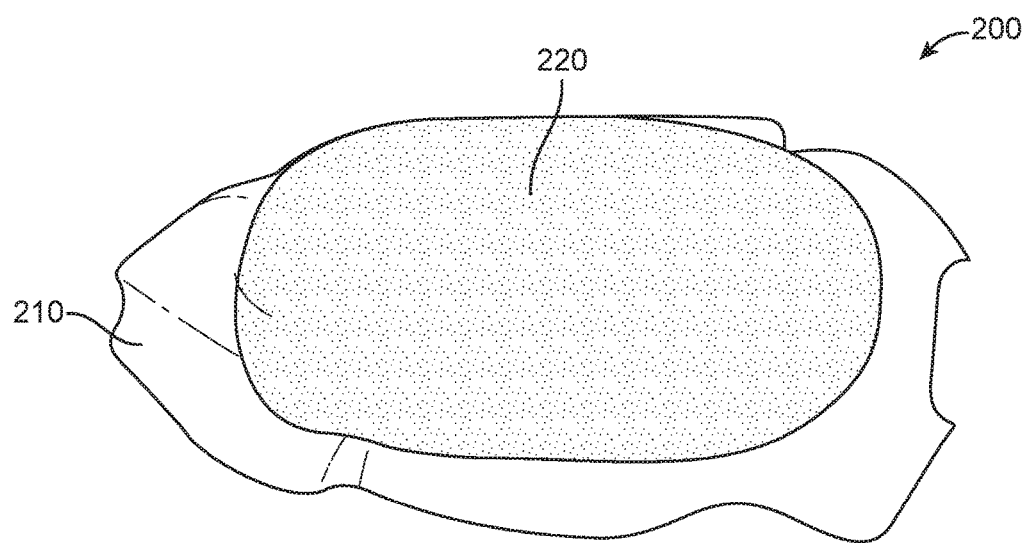
FIG. 2 is a diagram illustrating a second exemplary shave cream pod, according to the disclosure herein.

Films compatible for use as water-soluble enclosures can include, but are not limited to, natural water-soluble polymers, such as xanthan gum, pectins, chitosan derivatives, dextran, carrageenan, guar gum, cellulose ethers, hyaluronic acid, albumin, and starch or starch based derivatives; and synthetic water-soluble polymers, such as poly(ethylene glycol) (PEG), polyvinyl pyrrolidone (PVP), polyvinyl alcohol (PVA), polyacrylic acid (PAA), polyacrylamides, N-(2-hydroxypropyl) methacrylamide (HPMA), divinyl ether-maleic anhydride (DIVEMA), polyoxazoline, polyphosphates, and polyphosphazenes; or mixtures thereof. Suitable water-soluble films can be turned into an enclosure of any desired size or shape using a packing machine, such as, a PVA film packaging machine. For example, FIG. 1 illustrates a square shave cream pod 100 having a film enclosure 110 filled with a compatible shave cream formulation 120. In the alternative, FIG. 2 illustrates an elongated pod 200 having a film enclosure 210 and compatible shave cream formulation 220. While FIGS. 1 and 2 generally depict square and elongated film enclosures, it would be readily apparent to those skilled in the art that the film enclosure can be of any shape, as long as it is sealed on all sides to prevent leakage.

Figure 3:
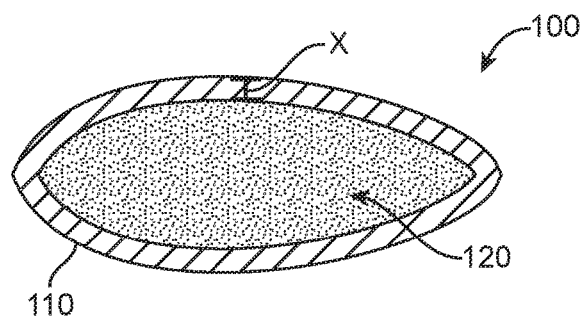
FIG. 3 is a cross sectional diagram of the shave cream pod of FIG. 1, taken along line A-A.

The film used in the pod can be any commercially available water-soluble film. Such films are commercially available from MonoSol®, Solublon®, CHBPack®, Ifhidro®, as well as other companies around the world. Water-soluble films can have a variety of adjustable properties, for example they can be produced in any thickness based on the desired use. The thickness of the film used in the shave cream pod is directly correlated to the speed with which the pod will dissolve. For example, FIG. 3 illustrates a cross sectional view of the square shave cream pod 100 of FIG. 1, wherein the film enclosure 110 has a thickness X. In at least one embodiment, the thickness X of the film can be from about 0.5 mm to about 10 mm, in at least some embodiments the thickness X of the film can be from about 1 mm to about 5 mm. As the thickness of the film decreases, so does the speed with which the pod will dissolve. The thickness required for the film used in the shave cream pod can also be affected by the shave cream formulation. Specifically, the pH of the shave cream formulation must be compatible with the water-soluble film used to form the enclosure. For example, for the shave cream formulation to be compatible for use with a water-soluble film, the shave cream formulation must have a pH between about 5 and about 11. In at least one embodiment, the present shave cream has a pH of from about 7 to about 10. As stated above, an optional pH adjusting material can be present in the formulation to help achieve the necessary pH.

One embodiment of the present shave cream formulation was tested for film compatibility using a PVA resin blend film and a shave cream having a water content of about 8 weight percent water, based on total weight of the formulation, and a pH of 8.1. The film used during testing was 1.5 mm thick; it should be noted that as the enclosure is filled with the shave cream formulation, the film can be stretched, such that the film becomes thinner. Thus, the pod produced by the film can have a thickness of less than 1.5 mm at various points, depending how the material stretched during filling.

During testing, ten shave cream pods were produced and split into three groups. Each group was placed into a sealed jar and each jar was subjected to various environments. Four shave cream pods were subjected to ambient temperature and humidity (23° C., 50% RH), four shave cream pods were subjected to increased temperature and humidity (38° C. and 80% RH), and the remaining two shave cream pods were subjected to increased temperature and reduced humidity (38° C. and 10% RH). Multiple tests were performed to determine compatibility of the shave crema with a water-soluble film pod over a set period of time. A first test measured complete solubility of the film and a second test measured disintegration of the film. Results of the tests are shown in Tables 1 and 2, below. Table 1 demonstrates the time, in seconds, for complete solubility of a Vivos® LXP9643 water-soluble film in distilled water at a temperature of 10° C.

TABLE 1

| | Time to Complete Solubility (Seconds) | | | |
|---|---|---|---|---|
| | Unexposed | 14 Days | 28 Days | 42 Days |
| Ambient Temp./Humidity | 30 | 43 | 45 | 37 |
| 38 C., 80% RH | 38 | 44 | 51 | 51 |
| 38 C., 10% RH | 30 | N/A | N/A | 50 |

The solubility of the film was measured periodically for each of the three environments. Specifically, the solubility of the film for each of the groups that contained four pods was tested prior to environmental exposure and after exposure at intervals of 14, 28, and 42 days. The final group was only tested prior to exposure and after 42 days. The test was performed by dissolving the shave cream pod in distilled water at 10 C, the time required to dissolve the pod was timed and recorded. As shown in Table 1, the film solubility remained roughly consistent, despite the change of surrounding environment. Table 2, below, demonstrates the time, in seconds, for full disintegration of a Vivos® LXP9643 water-soluble film in distilled water at a temperature of 10° C.

TABLE 2

| | Time to Disintegration (Seconds) | | | |
|---|---|---|---|---|
| | Unexposed | 14 Days | 28 Days | 42 Days |
| Ambient Temp./Humidity | 17 | 17 | 17 | 16 |
| 38 C., 80% RH | 17 | 18 | 18 | 17 |
| 38 C., 10% RH | 17 | N/A | N/A | 18 |

Disintegration tests were performed in the same manner as the solubility tests described above. As shown in Table 2, the environment and duration had little effect on the disintegration time of the shave cream pod. Thus, the shave cream formulation was found to be compatible with the water-soluble film enclosure.

While the embodiments have been described in detail in the foregoing description, the same is to be considered as illustrative and not restrictive in character, it being understood that only some embodiments have been shown and described and that all changes and modifications that come within the spirit of the embodiments are desired to be protected.

Numerous examples are provided herein to enhance understanding of the present disclosure. A specific set of statements are provided as follows.

Statement 1: A shave cream formulation comprising one or more surfactants; one or more emulsifying agents; and water, wherein the water is present in an amount of less than twenty (20) weight percent, based on total weight of the formulation.

Statement 2: A shave cream formulation in accordance with Statement 1, wherein the one or more surfactants are oil soluble.

Statement 3: A shave cream formulation in accordance with Statement 1 or Statement 2, wherein the one or more surfactants are selected from ammonium laureth sulfate, ammonium lauryl sulfate, steric acid, triethanolamine myristate, triethanolamine stearate, sodium olefin sulfonate, palmitic acid, sodium laureth sulfate, sodium lauryl sulfate, disodium laureth sulfosuccinate, sodium lauroamphoacetate, laureths 1-23, lauryl glucoside, palm kernel acid, waxes, cocamides, diethanolamine, disodium polyethylene glycol-4-cocoamido monoisopropanolamine sulfosuccinate, lanolin derivatives, coconut acids, polyquaternium compounds, or combinations thereof.

Statement 4: A shave cream formulation in accordance with Statements 1-3, further comprising one or more additives selected from fragrance, preservatives, pH adjusting materials, colorants, plant extracts, essential oil derivatives, antioxidants, and vitamins, or combinations thereof.

Statement 5: A shave cream formulation in accordance with Statements 1-4, wherein the pH adjusting material provides a pH of from about 5 to about 11.

Statement 6: A shave cream formulation in accordance with Statements 1-5, wherein the pH is from about 7 to about 10.

Statement 7: A shave cream formulation in accordance with Statements 1-6, wherein the pH is about 8.

Statement 8: A shave cream formulation in accordance with Statements 1-7, wherein the water content is less than fifteen (15) percent, based on total weight of the formulation.

Statement 9: A shave cream formulation in accordance with Statements 1-8, wherein the water content is less than eight (8) percent, based on the total weight of the formulation.

Statement 10: A shave cream formulation in accordance with Statements 1-9, wherein the one or more surfactants are present in an amount of more than fifteen (15) weight percent, based on the total weight of the formulation.

Statement 11: A shave cream formulation in accordance with Statements 1-10, wherein the one or more emulsifying agents are present in an amount of from about five (5) weight percent to about forty (40) weight percent, based on the total weight of the formulation.

Statement 12: A shave cream formulation in accordance with Statements 1-11, further comprising a humectant present in an amount of from about five (5) weight percent to about twenty (20) weight percent, based on the total weight of the formulation.

Statement 13: A shave cream formulation in accordance with Statements 1-12, further comprising a cleansing agent present in an amount of less than about forty (40) weight percent, based on the total weight of the formulation.

Statement 14: A shave cream pod comprising an enclosure made of a water-soluble film, and a shaving cream formulation disposed within the enclosure, the shaving cream formulation comprising one or more surfactants, one or more emulsifying agents, and water, wherein the water is present in an amount of less than twenty (20) weight percent, based on total weight of the formulation.

Statement 15: A shave cream pod in accordance with Statement 14, wherein the water-soluble film has a thickness of less than about 5 mm.

Statement 16: A shave cream pod in accordance with Statement 14 or Statement 15, wherein the water-soluble film comprises one or more natural water-soluble polymers, one or more synthetic water-soluble polymers, or a combination thereof.

Statement 17: A shave cream pod in accordance with Statements 14-16, wherein the one or more surfactants in the shaving cream formulation are oil soluble.

Statement 18: A shave cream pod in accordance with Statements 14-17, wherein the one or more surfactants in the shaving cream formulation are selected from ammonium laureth sulfate, ammonium lauryl sulfate, steric acid, triethanolamine myristate, triethanolamine stearate, sodium olefin sulfonate, palmitic acid, sodium laureth sulfate, sodium lauryl sulfate, disodium laureth sulfosuccinate, sodium lauroamphoacetate, laureths 1-23, lauryl glucoside, palm kernel acid, waxes, cocamides, diethanolamine, disodium polyethylene glycol-4-cocoamido monoisopropanolamine sulfosuccinate, lanolin derivatives, coconut acids, polyquaternium compounds, or combinations thereof.

Statement 19: A shave cream pod in accordance with Statements 14-18, wherein the shaving cream formulation further comprises one or more additives selected from fragrance, preservatives, pH adjusting materials, colorants, plant extracts, essential oil derivatives, antioxidants, and vitamins, or combinations thereof.

Statement 20: A shave cream pod in accordance with Statements 14-19, wherein the pH adjusting material provides a pH of from about 5 to about 11.

Statement 21: A shave cream pod in accordance with Statements 14-20, wherein the pH is from about 7 to about 10.

Statement 22: A shave cream pod in accordance with Statements 14-21, wherein the pH is about 8.

Statement 23: A shave cream pod in accordance with Statements 14-22, wherein the water content of the shaving cream formulation is less than fifteen (15) percent, based on total weight of the formulation.

Statement 24: A shave cream pod in accordance with Statements 14-23, wherein the water content of the shaving cream formulation is less than eight (8) percent, based on total weight of the formulation.

Statement 25: A shave cream pod in accordance with Statements 14-24, wherein the one or more surfactants are present in an amount of more than fifteen (15) weight percent, based on a total weight of the formulation.

Statement 26: A shave cream pod in accordance with Statements 14-25, wherein the one or more emulsifying agents are present in an amount of from about five (5) weight percent to about forty (40) weight percent, based on the total weight of the formulation.

Statement 27: A shave cream pod in accordance with Statements 14-26, wherein the shave cream formulation further comprises a humectant present in an amount of from about five (5) weight percent to about twenty (20) weight percent, based on the total weight of the formulation.

Statement 28: A shave cream pod in accordance with Statements 14-27, wherein the shave cream formulation further comprises a cleansing agent present in an amount of less than about forty (40) weight percent, based on the total weight of the formulation.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and composition within the principles of the present disclosure to the full extent indicated by the broad general meaning of the terms used in the attached claims. It will therefore be appreciated that the embodiments described above may be modified within the scope of the appended claims.

What is claimed is:

1. A shaving cream formulation comprising:
   one or more surfactants, present in the amount of over fifty (50) percent by weight, based on a total weight of the formulation, wherein at least one of the one or more surfactants is selected from the group consisting of triethanolamine myristate and triethanolamine stearate, and is present in an amount of over fifteen (15) percent by weight based on a total weight of the formulation;
   one or more emulsifying agents, present in the amount of from about five (5) to about forty (40) percent by weight, based on the total weight of the formulation; and
   water,
   wherein water is present in an amount of from about one (1) weight percent to about fifteen (15) weight percent, based on the total weight of the formulation.

2. The shaving cream formulation of claim 1, wherein the one or more surfactants are oil soluble.

3. The shaving cream formulation of claim 1, wherein at least one of the one or more surfactants is selected from ammonium laureth sulfate, ammonium lauryl sulfate, stearic acid, sodium olefin sulfonate, palmitic acid, sodium laureth sulfate, sodium lauryl sulfate, disodium laureth sulfosuccinate, sodium lauroamphoacetate, laureths 1-23, lauryl glucoside, palm kernel acid, waxes, cocamides, diethanolamine, disodium polyethylene glycol-4-cocoamido monoisopropanolamine sulfosuccinate, lanolin derivatives, coconut acids, polyquaternium compounds, or combinations thereof.

4. The shaving cream formulation of claim 1, further comprising one or more additives selected from fragrance, preservatives, pH adjusting materials, colorants, plant extracts, essential oil derivatives, antioxidants, and vitamins, or combinations thereof.

5. The shaving cream formulation of claim 4, wherein the pH adjusting material provides a pH of from about 5 to about 11.

6. The shaving cream formulation of claim 5, wherein the pH is from about 7 to about 10.

7. A shave cream pod comprising:
   an enclosure made of a water-soluble film, and
   a shaving cream formulation disposed within the enclosure, the shaving cream formulation comprising:
      one or more surfactants, present in the amount of over fifty (50) percent by weight, based on a total weight of the formulation, wherein at least one of the one or more surfactants is selected from the group consisting of triethanolamine myristate and triethanolamine stearate, and is present in an amount of over fifteen (15) percent by weight based on a total weight of the formulation,
      one or more emulsifying agents, present in the amount of from about five (5) to about forty (40) percent by weight, based on the total weight of the formulation, and
      water,
      wherein water is present in an amount of from about one (1) weight percent to about fifteen (15) weight percent, based on the total weight of the formulation.

8. The shave cream pod of claim 7, wherein the water-soluble film has a thickness of less than about 5 mm.

9. The shave cream pod of claim 7, wherein the one or more surfactants in the shaving cream formulation are oil soluble.

10. The shave cream pod of claim 7, wherein at least one of the one or more surfactants in the shaving cream formulation are selected from ammonium laureth sulfate, ammonium lauryl sulfate, steric acid, sodium olefin sulfonate, palmitic acid, sodium laureth sulfate, sodium lauryl sulfate, disodium laureth sulfosuccinate, sodium lauroamphoacetate, laureths 1-23, lauryl glucoside, palm kernel acid, waxes, cocamides, diethanolamine, disodium polyethylene glycol-4-cocoamido monoisopropanolamine sulfosuccinate, lanolin derivatives, coconut acids, polyquaternium compounds, or combinations thereof.

11. The shave cream pod of claim 7, wherein the shaving cream formulation further comprises one or more additives selected from fragrance, preservatives, pH adjusting materials, colorants, plant extracts, essential oil derivatives, antioxidants, and vitamins, or combinations thereof.

12. The shaving cream pod of claim 11, wherein the pH adjusting material provides a pH of from about 5 to about 11.

13. The shaving cream pod of claim 12, wherein the pH is from about 7 to about 10.

14. The shave cream pod of claim 7, wherein the water-soluble film comprises one or more natural water-soluble polymers, one or more synthetic water-soluble polymers, or a combination thereof.

15. The shaving cream formulation of claim 1, wherein water is present in an amount of from about one (1) weight percent to about eight (8) weight percent, based on the total weight of the formulation.

16. The shaving cream formulation of claim 3, wherein at least one of the one or more surfactants is selected from steric acid and sodium olefin sulfonate.

17. The shaving cream pod of claim 7, wherein water is present in an amount of from about one (1) weight percent to about eight (8) weight percent, based on the total weight of the formulation.

18. The shaving cream pod of claim 10, wherein at least one of the one or more surfactants is selected from steric acid and sodium olefin sulfonate.

\* \* \* \* \*